United States Patent

Chariot et al.

[11] Patent Number: 6,165,507
[45] Date of Patent: Dec. 26, 2000

[54] SLOW-RELEASE PHARMACEUTICAL FORMULATIONS CONTAINING MIZOLASTINE

[75] Inventors: Maryvonne Chariot, La Ville du Bois; Gareth Lewis, Dourdan; Jean Montel, Chatou, all of France

[73] Assignee: Synthelabo, Le Plessis Robinson, France

[21] Appl. No.: 09/125,810

[22] PCT Filed: Feb. 28, 1997

[86] PCT No.: PCT/FR97/00355

§ 371 Date: Aug. 26, 1998

§ 102(e) Date: Aug. 26, 1998

[87] PCT Pub. No.: WO97/32584

PCT Pub. Date: Sep. 12, 1997

[30] Foreign Application Priority Data

Mar. 4, 1996 [FR] France ................. 96 02662

[51] Int. Cl.[7] ................. A61K 9/22; A61K 9/36; A61K 9/14; A61K 31/505

[52] U.S. Cl. ................. 424/468; 424/480; 424/484; 514/272

[58] Field of Search ................. 424/472, 474, 424/484, 468

[56] References Cited

U.S. PATENT DOCUMENTS 5,681,583  10/1997  Conte et al. ................. 424/472
5,686,105  11/1997  Kelm et al. ................. 424/452

FOREIGN PATENT DOCUMENTS 0 217 700  8/1987  European Pat. Off. .

OTHER PUBLICATIONS

Derwent. Mosques, R. et al. Antihistamines for the treatment of nasal congestion. Allergy. 51(31):157, 1996.
Chemical Abstracts, vol. 107, No. 1, 1987, Abstract No. 7211.

*Primary Examiner*—Thurman K. Page
*Assistant Examiner*—Alysia Berman
*Attorney, Agent, or Firm*—Jacobson, Price, Holman & Stern, PLLC

[57] ABSTRACT

A sustained-release pharmaceutical formulation containing mizolastine, a core formed of a sustained-release table containing mizolastine combined with a fatty matrix and an organic acid, the tablet being coated.

5 Claims, 3 Drawing Sheets

FIG. 4
Table 1

| Formulation | Tmax (h) | Cmax (ng/ml) | t1/2β (h) | AUC (0–∞) (ng.ml$^{-1}$.h) | Frel |
|---|---|---|---|---|---|
| Gelatin capsule | 0.9 | 398.4±22.7 | 14.8±1.5 | 1481±96 | |
| Min–Max | 0.5–1.5 | 202–529 | 6.7±33.1 | 1092–2717 | |
| Tablet | 1.4 | 234.2±13.7 | 14.5±1.2 | 1406.1±119 | 0.962 |
| Min–Max | 0.5–2.5 | 154–393 | 6.7–26.4 | 775–2458 | |
| Statistical comparison | NS | p<0.001 | NS | NS | |

FIG. 5
Table 2

| Formulation | Tmax (h) | Cmax (ng/ml) | t1/2β (h) | AUC (0–t) (ng.ml$^{-1}$.h) | AUC (0–∞) (ng.ml$^{-1}$.h) | Frel |
|---|---|---|---|---|---|---|
| With L-tartaric acid | 1.00 | 243.7±12.7 | 13.1±1.2 | 1347±117 | 1444±125 | |
| Min–Max | 0.75–2.5 | 166.5–314.1 | 5.9±19.4 | 734–1878 | 773–2011 | |
| Without L-tartaric acid | 0.75 | 147.0±28.8 | 12.9±1.1 | 601±134 | 635±139 | 0.43±0.08 |
| Min–Max | 0.5–2.5 | 4.5–285.4 | 5.1–17.6 | 27–1347 | 38–1397 | 0.03–0.87 |
| Statistical comparison | NS | p<0.05 | NS | p<0.01 | p<0.01 | |

SLOW-RELEASE PHARMACEUTICAL FORMULATIONS CONTAINING MIZOLASTINE

The present invention relates to novel sustained-release pharmaceutical formulations containing 2-[[1-[1-[(4-fluorophenyl)methyl]-1H-benzimidazol-2-yl]piperid-4-yl] methylamino]-pyrimidin-4-ol or 2-[[1-[1-[(4-fluorophenyl) methyl]-1H-benzimidazol-2-yl]piperid-4-yl]methylamino]-pyrimidine-4(1H)-one, or mizolastine, as active principle.

Mizolastine is described in European patent EP 0,217,700.

Mizolastine binds to the $H_1$ histamine receptor and inhibits the degranulation of mastocytes in vitro and in vivo. It can thus be used for the treatment of respiratory, cutaneous or ocular allergies and various allergic manifestations.

During the oral administration of immediate-release formulations containing mizolastine, undesirable sedative effects have been observed which are associated with the existence of a high peak in the plasma.

Consequently, it was necessary to find formulations for an oral administration which have a profile of release of the active principle such that it is possible to obtain a lower peak in the plasma without decreasing the bioavailability.

Applicant have based their research of such formulations on the study of the kinetics of dissolution of mizolastine. The reason for this is that mizolastine is a weak base (pK 5.6) which is sparingly soluble in water (13 mg/l at neutral pH) but much more soluble at acidic pH (11 g/l at pH 3); the first gelatin capsules released 100% of mizolastine over 30 minutes in a dissolution medium at pH 2 whereas only 40% were dissolved at pH 6.8.

Moreover, the release of mizolastine from the sustained-release pharmaceutical form according to the invention did not need to be influenced by the differences in pH in the gastrointestinal tract.

The aim of the present invention is to propose formulations containing mizolastine whose dissolution profile is as follows:

about 30 to 70% of mizolastine dissolved in 1 hour,
100% of mizolastine dissolved in 3 to 5 hours, and
pH-independent profile.

Applicants have shown that tablets containing a core formed of a sustained-release tablet containing mizolastine combined with a fatty matrix and with an organic acid, the said tablet being coated to prevent degradation of the product by light, are entirely suitable.

FIG. 1 shows the dissolution profile obtained with a formulation according to the invention;

FIG. 2 shows the dissolution profiled obtained with a formulation identical to that of the invention but containing no L-tartaric acid; and FIG. 3 shows the curves of the plasma kinetics of a pharmaceutical form according to the invention containing 10 mg of mizolastine studied in a healthy volunteer after a single oral administration, compared with a standard immediate-release gelatin capsule containing 10 mg of mizolastine.

FIG. 4 present the kinetic parameters of the plasma kinetics in table form.

FIG. 5 provides a tabular comparison of the bioavailability of the formulations with and without L-tartaric acid.

DETAILED DESCRIPTION OF THE INVENTION

The tablets according to the invention contain from 1 mg to 25 mg of mizolastine. These doses correspond to concentrations of from 0.5% to 12% by weight of mizolastine.

The fatty matrix is made with hydrogenated castor oil or with hydrogenated lecithins or long-chain fatty acids, for example $C_{12}$–$C_{28}$ long chain fatty acids such as behenic acid, or triglycerides esterified with medium-chain fatty acids, for example $C_8$–$C_{18}$ fatty acids.

The organic acid preferably having a pK of 2 or more is chosen from maleic, tartaric, malic, fumaric, lactic, citric, adipic and succinic acids in the form of racemates or isomers. According to the invention, the acid particularly preferred is L-tartaric acid.

The weight ratio between the mizolastine and the organic acid should be between 0.3 and 1. With L-tartaric acid, this ratio is preferably equal to 0.5.

The tablets are prepared by granulation using the active principle, the agent constituting the fatty matrix, the organic acid and other excipients such as, for example, lactose, mannitol and sugars or similar sugar-alcohols, microcrystalline cellulose, starch, calcium phosphates and sulphates, polyvidone, and substituted celluloses such as hydroxypropyl-cellulose, hydroxypropylmethylcellulose or methylcellulose.

The granulation may be carried out in a wet phase, for example in the presence of water or alcohol, or may be performed by fusion or by compacting. The granulation step may optionally be left out and the tablets prepared by direct tableting of the mixture of mizolastine and the excipients.

Anhydrous colloidal silica and magnesium stearate are added to the granules obtained and the mixture is tableted. The tablets are then covered with a coating film by spraying them with a coating solution in a machine with a fluidized-air bed or in a coating turbine.

The example which follows illustrates the invention without limiting it:

| Tablet | % (weight) |
|---|---|
| mizolastine | 4.8 |
| hydrogenated castor oil | 12.0 |
| lactose | 60.0 |
| microcrystalline cellulose | 9.6 |
| L-tartaric acid | 9.6 |
| polyvidone | 2.9 |
| anhydrous colloidal silica | 0.2 |
| magnesium stearate | 0.9 |
| purified water | Q.S. |
| Total | 100.0 |

| Coating | |
|---|---|
| methylhydroxypropylcellulose | 74.0 |
| titanium dioxide (E171) | 18.5 |
| propylene glycol | 7.5 |
| purified water | Q.S. |
| Total | 100.0 |

Figure 1:
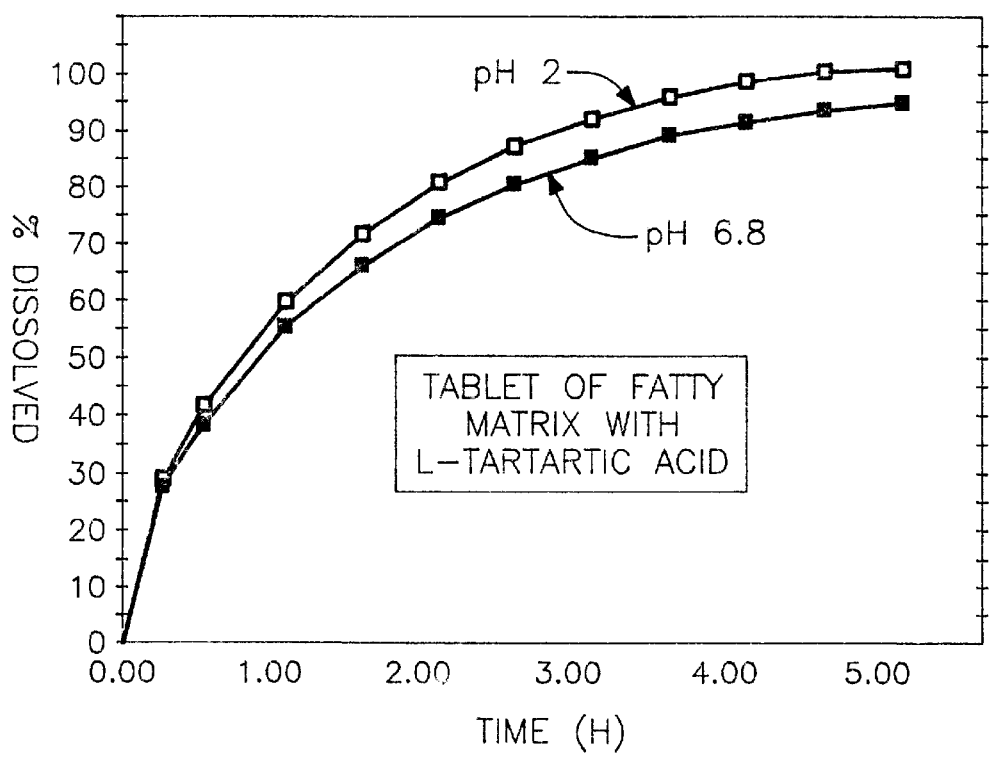

The dissolution profile obtained with a formulation according to the invention is given in FIG. 1.

This profile gives about 50% of product dissolved in 1 hour, 100% of product dissolved in 3 to 5 hours, and it is independent of the pH.

Figure 2:
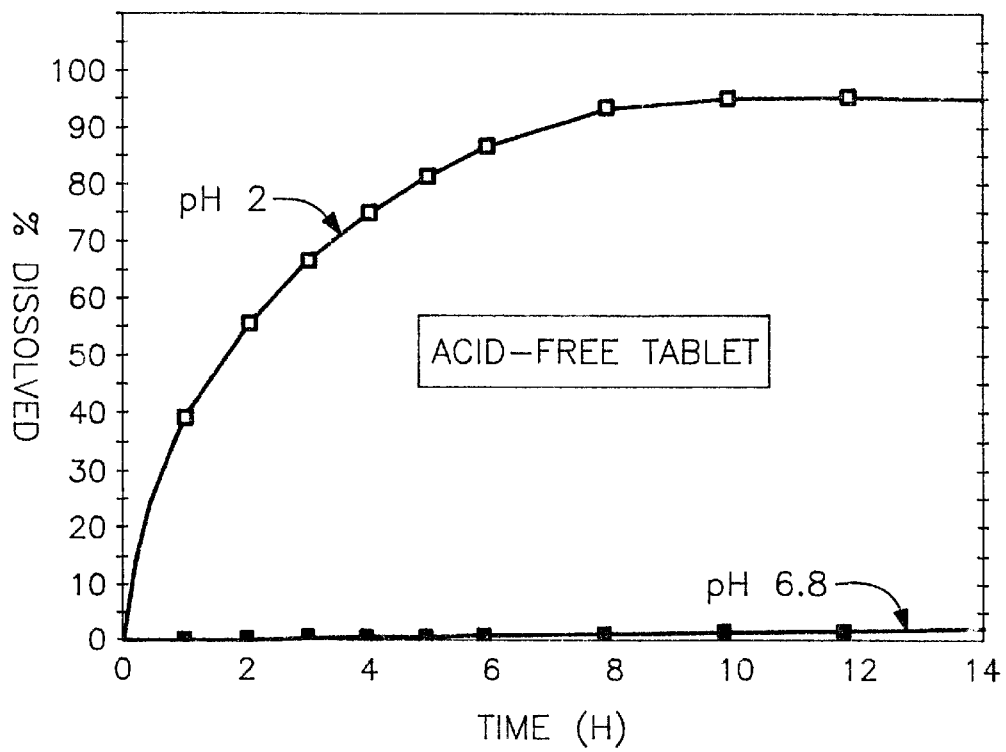

The dissolution profile obtained with a formulation identical to that of the invention but containing no L-tartaric acid is given in FIG. 2.

The plasma kinetics of a pharmaceutical form according to the invention containing 10 mg of mizolastine were studied in a healthy volunteer after a single oral administration, compared with a standard immediate-release gelatin capsule containing 10 mg of mizolastine.

Figure 3:
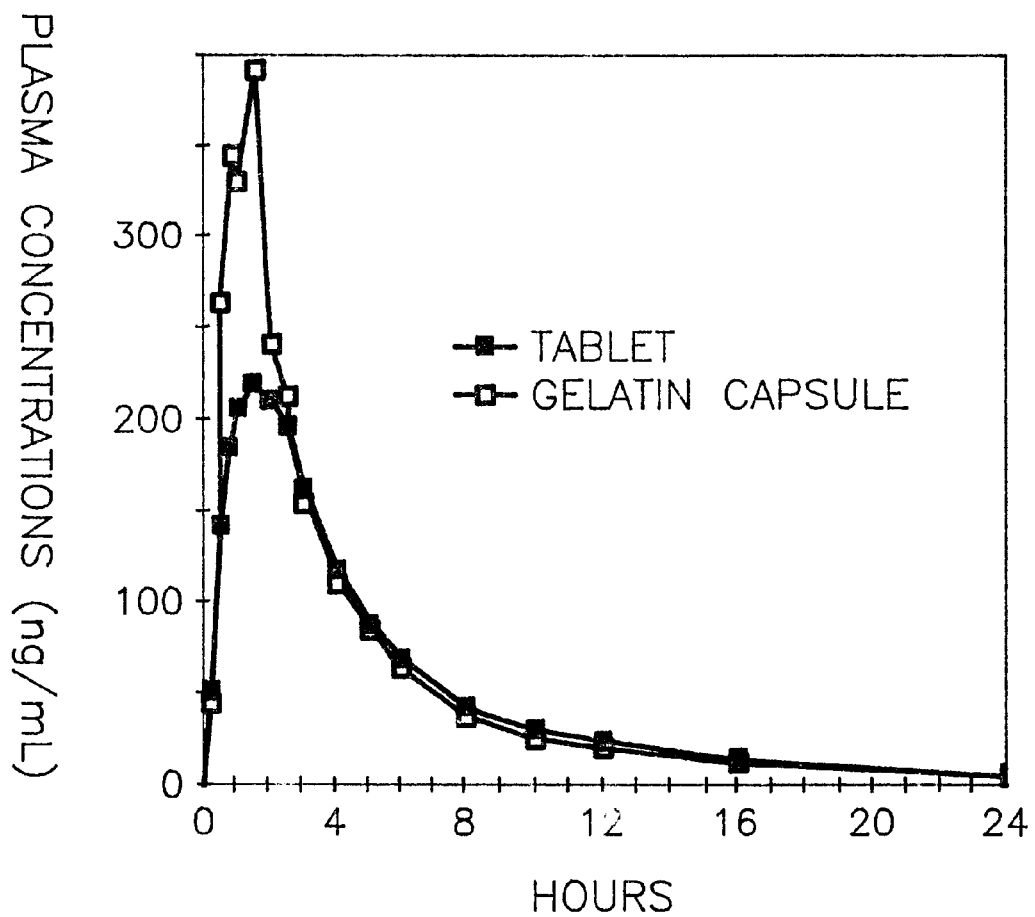

FIG. 4 (Table 1) presents the kinetic parameters and FIG. 3 the curves of the plasma kinetics, obtained respectively with each formulation; the plasma kinetics obtained with the pharmaceutical form according to the invention makes it possible to prevent any peak in the plasma without losing bioavailability.

The plasma kinetics of a pharmaceutical form according to the invention were also studied in comparison with the same formulation without L-tartaric acid.

The study was performed on twelve healthy volunteers after a single oral administration of a tablet according to the invention containing 10 mg of mizolastine or the same tablet without L-tartaric acid.

FIG. 5 (Table 2) shows that the bioavailability of the formulation containing no L-tartaric acid represents only 43% of that observed with the formulation according to the invention containing L-tartaric acid. The values of Cmax and the AUC values (0–∞) are respectively 1.5 and 2 times as high for the formulation containing L-tartaric acid as for that not containing any.

In addition, for the formulation with L-tartaric acid, the min.–max. variation indices are much lower, which suggests great uniformity in the release.

The results altogether show that the formulations according to the invention have:

a pH-independent dissolution profile, an in vivo release which prevents any peak in the plasma, a bioavailability which is not decreased relative to an immediate-release formulation, lower variability of the plasma kinetics results.

What is claimed is:

1. Coated sustained release tablet, consisting essentially of mizolastine, a fatty matrix, an organic acid, and a coating, the coated tablet having a dissolution profile which is pH independent, the fatty matrix being selected from the group consisting of hydrogenated castor oil, a hydrogenated lecithin, a long-chain fatty acid and a triglyceride esterified with one, two or three medium-chain fatty acids, the organic acid being selected from the group consisting of maleic, tartaric, malic, fumaric, lactic, citric, adipic and succinic acid in the form of a racemate or an isomer.

2. Coated sustained release tablet of claim 1, wherein the tablet contains 0.5% to 12% by weight of the mizolastine and the weight ratio between the mizolastine and the organic acid is between 0.3 and 1.

3. Coated sustained release tablet of claim 2, wherein the tablet further contains excipients selected from the group consisting of lactose, mannitol, microcrystalline cellulose, starch, calcium phosphate, calcium sulphate, polyvidone, hydroxypropyl-cellulose, hydroxypropylmethylcellulose and methylcellulose.

4. Coated sustained release tablet of claim 3, wherein the tablet contains by weight 4.8% mizolastine, 12% hydrogenated castor oil, 60% lactose and 9.6% L-tartaric acid.

5. Coated sustained release tablet of claim 4, wherein the tablet further contains 9.6% microcrystalline cellulose.

* * * * *